United States Patent [19]

Drent et al.

[11] Patent Number: 5,206,342
[45] Date of Patent: Apr. 27, 1993

[54] POLYMERIZATION OF CARBON MONOXIDE/NON CONJUGATED ALKENYL BENZENE

[75] Inventors: Eit Drent; Eric Kragtwijk, both of CM Amsterdam, Netherlands

[73] Assignee: Shell Oil Company, Houston, Tex.

[21] Appl. No.: 808,832

[22] Filed: Dec. 17, 1991

[30] Foreign Application Priority Data

Feb. 28, 1991 [NL] Netherlands ............. 9100372

[51] Int. Cl.$^5$ ............................. C08G 67/02
[52] U.S. Cl. .................... 528/392; 528/205; 528/271
[58] Field of Search ............. 528/392, 205, 271

[56] References Cited

U.S. PATENT DOCUMENTS

| | | | |
|---|---|---|---|
| 4,788,279 | 11/1988 | Drent | 528/392 |
| 4,818,810 | 4/1989 | Drent | 528/392 |
| 4,843,144 | 6/1989 | Van Broekhoven et al. | 528/392 |
| 4,880,903 | 11/1989 | Van Broekhoven et al. | 528/392 |
| 4,940,775 | 6/1990 | Drent | 528/392 |
| 4,965,341 | 10/1990 | Van Doorn et al. | 528/392 |

FOREIGN PATENT DOCUMENTS

235865-A2  9/1987  European Pat. Off.
345847  12/1989  European Pat. Off.
410543-A2  1/1991  European Pat. Off.

*Primary Examiner*—Harold D. Anderson

[57] ABSTRACT

Linear alternating polymers of carbon monoxide, non-conjugated alkenylbenzene compound and optionally ethylene are produced by contacting the monomeric reactants under polymerization conditions in the presence of an inert reaction diluent and a catalytic quantity of a catalyst composition formed from a compound of palladium, the anion of a strong non-hydrohalogenic acid having a pKa less than 2 and a bis(dialkylphosphino)alkane. The polymer products are thermoplastics and have utility as engineering thermoplastics.

19 Claims, No Drawings

POLYMERIZATION OF CARBON MONOXIDE/NON CONJUGATED ALKENYL BENZENE

FIELD OF THE INVENTION

This invention relates to a process of producing a novel class of linear alternating polymers containing units derived from carbon monoxide and units derived from a non-conjugated alkenylbenzene compound. More particularly, the invention relates to the production of such polymers in the presence of a catalyst composition containing a tetraalkyl bidentate phosphorus ligand.

BACKGROUND OF THE INVENTION

The class of linear alternating polymers of carbon monoxide and ethylenically unsaturated compounds is now well known in the art. Such materials are characterized by a structure having the repeating formula

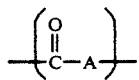
(I)

wherein A is a moiety of at least one ethylenically unsaturated compound polymerized through the ethylenic linkage thereof. Although the scope of the process of producing such polymers is extensive, the process typically comprises contacting the carbon monoxide and ethylenically unsaturated compound in the presence of a catalyst composition formed from a compound of a Group VIII metal, preferably selected from palladium, cobalt or nickel, the anion of a strong non-hydrohalogenic acid and a bidentate ligand of phosphorus, arsenic, antimony or nitrogen. For the polymerization of most ethylenically unsaturated hydrocarbons, a catalyst composition wherein the metal compound is a compound of palladium and the bidentate ligand is a ligand of phosphorus is preferred. See, for example, van Broekhoven et al, U.S. Pat. Nos. 4,880,903, and 4,843,144. In most cases, the use of a bidentate phosphorus ligand wherein each monovalent phosphorus substituent is aromatic is particularly preferred.

For the polymerization of certain ethylenically unsaturated compounds, the use of the generally preferred bis(diarylphosphino)alkane ligands does not give entirely satisfactory results. When linear alternating polymers of carbon monoxide and styrene are desired, it has been found that bidentate ligands of nitrogen such as 2,2'-bipyridine are preferred and bidentate phosphorus ligands are not suitable. See, for example, U.S. Pat. Nos. 4,788,279 and 4,965,341.

When linear alternating polymers of carbon monoxide and a non-conjugated alkenyl benzene compound such as allylbenzene are desired, it has been found that neither the bis(diarylphosphino)-alkane or the bidentate nitrogen ligands provides satisfactory results. It would be of advantage to provide a better process for the production of linear alternating polymers of non-conjugated alkenylbenzene compounds.

SUMMARY OF THE INVENTION

The present invention provides an improved process for the production of linear alternating polymers of carbon monoxide, non-conjugated alkenylbenzene compound and, optionally, ethylene. The linear alternating polymers are produced in the presence of a compound of palladium, the anion of a strong non-hydrohalogenic acid and a bis(dialkylphosphino)alkane ligand.

DESCRIPTION OF THE INVENTION

The polymers of the invention are linear alternating polymers containing units derived from carbon monoxide, units derived from a non-conjugated alkenylbenzene compound and, optionally, units derived from ethylene. The non-conjugated alkenylbenzene compound is characterized by an alkenyl group attached to an unsubstituted or substituted phenyl ring, wherein the ethylenic unsaturation of the alkenyl moiety is not conjugated with the aromatic unsaturation of the phenyl ring. Illustrative of the non-conjugated alkenylbenzene compounds are compounds of the formula

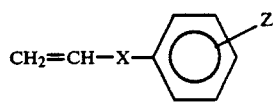
(II)

wherein X is a divalent alkylene group of from 1 to 10 carbon atoms inclusive and Z is hydrogen, hydroxy, alkoxy of up to 4 carbon atoms inclusive, alkyl of up to 4 carbon atoms inclusive, or amino. Such compounds include allylbenzene, 3-phenylbutene-1, 3-phenyloctene-1, 4-phenylpentene-1, 1-allyl-3-methylbenzene, 1-allyl-4-hydroxybenzene, 1-methallyl-4-aminobenzene and 1-allyl-3cyanobenzene. Preferred compounds of the above formula II are those hydrocarbon compounds wherein Z is hydrogen and particularly preferred is allylbenzene.

The linear alternating polymers are represented by the repeating formula

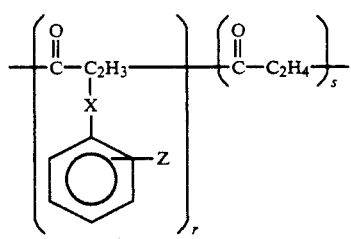
(III)

wherein the molar ratio of s:r is up to about 30. When copolymers of carbon monoxide and non-conjugated alkenylbenzene compound are produced, there will be no ethylene present and the copolymers are illustrated by the above formula III wherein s is zero. When terpolymers of carbon monoxide, non-conjugated alkenylbenzene compound and ethylene are produced, the units derived from non-conjugated alkenylbenzene compound and the units derived from ethylene are found randomly throughout the polymer chain and the preferred ratio of s:r is from about 5:1 to about 25:1. Although the terpolymers of the above formula III have a number of useful properties, the preferred polymers of the invention are copolymers of carbon monoxide and non-conjugated alkenylbenzene compound, especially copolymers of carbon monoxide and allylbenzene.

The polymers are produced by contacting the carbon monoxide, the non-conjugated alkenylbenzene compound and, optionally, ethylene, under polymerization conditions in the presence of an inert reaction diluent and a catalytic quantity of a catalyst composition formed from a compound of palladium, the anion of a non-hydrohalogenic acid having a pKa less than 2 and a bis(dialkylphosphino)alkane ligand. The palladium compound is preferably a palladium carboxylate and palladium acetate, palladium propionate, palladium butyrate and palladium hexanoate are satisfactory. Particularly preferred is palladium acetate. The anion of the non-hydrohalogenic acid is suitably the anion of an inorganic acid such as sulfuric acid or perchloric acid or the anion of an organic acid including carboxylic acids such as trifluoroacetic acid, difluoroacetic acid or trichloroacetic acid, as well as sulfonic acids such as methanesulfonic acid, p-toluenesulfonic acid or trifluoromethanesulfonic acid. The anion of sulfonic acids is generally preferred and particularly preferred is the anion of trifluoromethanesulfonic acid. The anion is suitably provided as the free acid but alternatively may be provided as a metal salt, particularly as the salt of a non-noble Group VIII metal, e.g., copper or nickel. The quantity of the anion to be employed is from about 1 mole to about 100 moles per mole of palladium. Preferred quantities of anion are from about 2 moles to about 50 moles of anion per mole of palladium.

The bis(dialkylphosphino)alkane bidentate ligand from which the catalyst composition is formed is illustrated by compounds of the formula

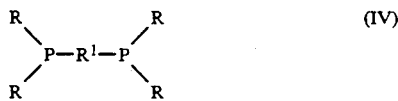

wherein R independently is alkyl of up to 10 carbon atoms inclusive and $R^1$ is a divalent hydrocarbon bridging group of up to 10 carbon atoms inclusive with from 2 to 4 carbon atoms in the bridge. Illustrative R groups are methyl, ethyl, propyl, isopropyl, butyl, sec-butyl, hexyl, octyl and decyl. Preferred R groups are straight-chain primary alkyl groups of up to 4 carbon atoms and particularly preferred are methyl and n-butyl. Suitable $R^1$ groups include 1,2-ethylene, 1,3-propylene, 1,4-butylene, 2-methyl-1,3propylene and 2,3-dimethyl-1,4-butylene. The preferred $R^1$ groups have 3 carbon atoms in the bridge and particularly preferred as the $R^1$ group is 1,3-propylene. The preferred bidentate ligands of the above formula IV are 1,3-bis(dimethylphosphino)propane and 1,3-bis(di-n-butylphosphino)propane. The bidentate ligand is suitably employed in a quantity from about 0.5 mole to about 2 moles per mole of palladium, preferably in a quantity from about 0.75 mole to about 1.5 mole per mole of palladium.

It is useful on occasion to additionally provide to the catalyst composition an organic oxidizing agent. Useful organic oxidizing agents include aliphatic nitrites such as butyl nitrite and amyl nitrite, aromatic nitro compounds such as nitrobenzene and nitrotoluene and hydroquinones. The 1,2-hydroquinones and 1,4-hydroquinones are satisfactory and are preferred as the organic oxidizing agent. Particularly preferred are 1,4-quinones such as 1,4-benzoquinone and 1,4-naphthoquinone, especially 1,4-naphthoquinone. As stated the presence of organic oxidizing agent is not required but amounts of organic oxidizing agent up to about 5,000 moles per mole of palladium are satisfactory. When oxidizing agent is present, amounts from about 10 moles to about 1,000 moles per mole of palladium are preferred.

The monomeric reactants and the catalyst composition are contacted in the presence of an inert reaction diluent under polymerization conditions. Useful reaction diluents include alkanols such as methanol and ethanol and alkanones such as acetone and methyl ethyl ketone. Alkanols are preferred reaction diluents, especially methanol. Typical reaction conditions include a temperature from about 20.C to about 150.C, preferably from about 30° C. to about 130° C. The reaction pressure is suitably from about 2 bar to about 150 bar although pressures from about 5 bar to about 100 bar are preferred.

The contacting of the carbon monoxide and ethylenically unsaturated reactant is conducted in a molar ratio of carbon monoxide to total unsaturated compound from about 10:1 to about 1:10, preferably from about 5:1 to about 1:5. The contacting takes place in the presence of a catalytic quantity of catalyst composition and in a suitable reactor and is facilitated by some means of agitation such as shaking or stirring.

The catalyst composition is employed in a catalytic quantity sufficient to provide from about $1 \times 10^{-7}$ mol to about $1 \times 10^{-3}$ mol of palladium per mol of total unsaturated reactant. Quantities of catalyst composition sufficient to provide from about $1 \times 10^{-6}$ mol to about $1 \times 10^{-4}$ mol of palladium per mol of total unsaturated reactant are preferred. Subsequent to reaction, the polymerization is terminated by cooling the reaction mixture and releasing the pressure. The polymer product is obtained as a material substantially insoluble in the media of its production. The polymer is recovered from the product mixture by conventional procedures such as filtration or decantation and is used as recovered or is purified by contact with a solvent or complexing agent which is selective for catalyst residues.

The linear alternating polymer products are thermoplastics having relatively high molecular weights and melting points and are useful as engineering thermoplastics. They are processed by methods conventionally employed for thermoplastic polymers, e.g., extrusion, injection molding and thermoforming, into a variety of shaped articles of established utility. Specific applications include the production of containers for food and drink and parts and housings for automotive applications.

The invention is further illustrated by the following Comparative Examples (not of the invention) and the Illustrative Embodiments which should not be regarded as limiting. The polymer produced in each Illustrative Embodiment was analyzed by $^{13}$C-NMR and found to be of a linear structure wherein units derived from carbon monoxide alternated with units derived from ethylenically unsaturated hydrocarbon. The polymer of Illustrative Embodiment II was found to contain the units derived from ethylene and allylbenzene in random order with about 10 units derived from ethylene for each unit derived from allylbenzene.

ILLUSTRATIVE EMBODIMENT I

A linear alternating copolymer of carbon monoxide and ethylene was produced by charging to a 250 ml autoclave equipped with a mechanical stirrer a catalyst composition solution comprising a mixture of 40 ml methanol, 0.25 mmol palladium acetate, 0.3 mmol 1,3-bis(dimethylphosphino)propane, 0.5 mmol nickel trifluoromethanesulfonate and 10 mmol 1,4-napthoquinone.

After 20 ml of allylbenzene was introduced into the autoclave the air present was removed by evacuation. Carbon monoxide was introduced until a pressure of 20 bar was reached and the autoclave and contents were heated to 70° C. After 1 hour, the polymerization was terminated by cooling the autoclave to room temperature and releasing the pressure. The polymer formed was recovered by filtration, washed with methanol and dried. The yield of copolymer was 20 g.

ILLUSTRATIVE EMBODIMENT II

A linear alternating terpolymer of carbon monoxide, ethylene and allylbenzene was obtained by a procedure substantially similar to that of Illustrative Embodiment I except that the catalyst composition solution contained 0.3 mmol of 1,3-bis(di-n-butylphosphino)propane as the bidentate phosphorus ligand, ethylene was additionally introduced into the autoclave to a pressure of 20 bar, and the reaction time was 0.5 hour instead of 1 hour. The yield of carbon monoxide/ethylene/allylbenzene terpolymer was 21 g.

ILLUSTRATIVE EMBODIMENT III

A linear alternating copolymer of carbon monoxide and allylbenzene was produced by a process substantially similar to that of Illustrative Embodiment I except that the catalyst composition solution contained 0.1 mmol of palladium acetate instead of 0.25 mmol and 0.12 mmol of 1,3-bis(dimethylphosphino)propane instead of 0.3 mmol, the reaction temperature was 50° C. instead of 70° C. and the reaction time was 3 hours instead of 1 hour. The yield of copolymer was 20 g.

ILLUSTRATIVE EMBODIMENT IV

A linear alternating copolymer of carbon monoxide and allylbenzene was produced by a process substantially similar to that of Illustrative Embodiment III except that the reaction time was 1.5 hour instead of 1 hour. The yield of copolymer was 21 g.

ILLUSTRATIVE EMBODIMENT V

A linear alternating copolymer of carbon monoxide and allylbenzene was produced by a procedure substantially similar to that of Illustrative Embodiment IV except that the reaction temperature was 20° C. instead of 50° C. and the reaction time was 10 hours instead of 1.5 hours. The yield of copolymer was 16 g.

COMPARATIVE EXAMPLE I

The procedure of illustrative Embodiment I was reported except that the catalyst composition solution contained 3 mmol of 2,2'-bipyridine instead of 1,3-bis(dimethylphosphino)propane and the time the autoclave and contents were maintained at elevated temperature was 5 hours instead of 1 hour. No polymer was produced.

COMPARATIVE EXAMPLE II

The procedure of Illustrative Embodiment I was repeated except that 0.3 mmol of 1,3-bis(di-n-butylphosphino)propane was employed instead of 1,3-bis(dimethylphosphino)propane, 20 ml of styrene was added to the autoclave instead of allylbenzene and the time of heating the autoclave and contents was 5 hours instead of 1 hour. No polymer was formed.

What is claimed is:

1. A process for the production of linear alternating polymers of carbon monoxide, a non-conjugated alkenylbenzene compound, with or without ethylene, by contacting carbon monoxide and the non-conjugated alkenylbenzene compound, with or without ethylene, under polymerization conditions in the presence of an inert reaction diluent and a catalytic quantity of a catalyst composition formed from a compound of palladium, the anion of a non-hydrohalogenic acid having a pKa less than 2 and a bis(dialkylphosphino)alkane.

2. The process of claim 1 wherein the non-conjugated alkenylbenzene compound is of the formula

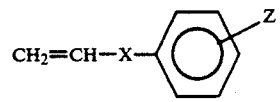

wherein X is divalent alkylene of from 1 to 10 carbon atoms inclusive and Z is hydrogen, hydroxy, alkoxy of up to 4 carbon atoms inclusive, alkyl of up to 4 carbon atoms inclusive or amino.

3. The process of claim 2 wherein the compound of palladium is palladium carboxylate.

4. The process of claim 3 wherein the bis(dialkylphosphino)alkane is of the formula

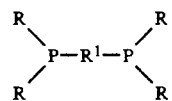

wherein R independently is alkyl of up to 10 carbon atoms inclusive and $R^1$ is a divalent hydrocarbon bridging group of up to 10 carbon atoms inclusive with from 2 to 4 carbon atoms in the bridge.

5. The process of claim 4 wherein the linear alternating polymer is represented by repeating units of the formula

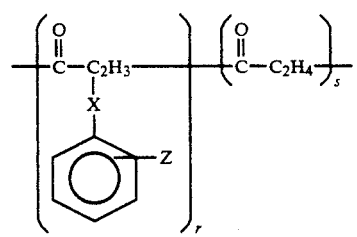

wherein X is a divalent alkylene group of from 1 to 10 carbon atoms inclusive, Z is hydrogen, hydroxy, alkoxy of up to 4 carbon atoms inclusive, alkyl of up to 4 carbon atoms inclusive, or amino, and the molar ratio of s:r is up to about 30.

6. The process of claim 5 wherein s is 0.

7. The process of claim 6 wherein R independently is straight-chain alkyl of up to 4 carbon atoms inclusive and $R^1$ is 1,3-propylene.

8. The process of claim 7 wherein the palladium carboxylate is palladium acetate.

9. The process of claim 8 wherein the anion is the anion of an organic sulfonic acid.

10. The process of claim 9 wherein each R is methyl or butyl.

11. The process of claim 10 wherein R is butyl.

12. The process of claim 11 wherein the anion is the anion of trifluoromethanesulfonic acid.

13. The process of claim 5 wherein the molar ratio of s:r is from about 5:1 to about 25:1.

14. The process of claim 13 wherein R independently is straight-chain alkyl of up to 4 carbon atoms inclusive and $R^1$ is 1,3-propylene.

15. The process of claim 14 wherein the palladium carboxylate is palladium acetate.

16. The process of claim 15 wherein the anion is the anion of an organic sulfonic acid.

17. The process of claim 16 wherein each R is methyl or butyl.

18. The process of claim 17 wherein R is butyl.

19. The process of claim 18 wherein the anion is the anion of trifluoromethanesulfonic acid.

* * * * *